(12) United States Patent
Dolley-Sonneville et al.

(10) Patent No.: US 10,900,021 B2
(45) Date of Patent: Jan. 26, 2021

(54) DRYING FORMULATION FOR HYDROGEL MICROCARRIERS

(71) Applicant: Corning Incorporated, Corning, NY (US)

(72) Inventors: Paula Jean Dolley-Sonneville, Corning, NY (US); David Henry, Fontaine le Port (FR); Jeffery Joseph Scibek, Horseheads, NY (US); Yue Zhou, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/579,776

(22) PCT Filed: Jun. 8, 2016

(86) PCT No.: PCT/US2016/036464
§ 371 (c)(1),
(2) Date: Dec. 5, 2017

(87) PCT Pub. No.: WO2016/200954
PCT Pub. Date: Dec. 15, 2016

(65) Prior Publication Data
US 2018/0171301 A1    Jun. 21, 2018

Related U.S. Application Data

(60) Provisional application No. 62/172,449, filed on Jun. 8, 2015.

(51) Int. Cl.
*C12N 5/0775* (2010.01)
*C12N 5/00* (2006.01)

(52) U.S. Cl.
CPC ......... *C12N 5/0663* (2013.01); *C12N 5/0075* (2013.01); *C12N 2500/34* (2013.01); *C12N 2500/62* (2013.01); *C12N 2500/99* (2013.01); *C12N 2531/00* (2013.01); *C12N 2533/40* (2013.01); *C12N 2537/00* (2013.01); *C12N 2537/10* (2013.01)

(58) Field of Classification Search
CPC .................................................. C12N 5/0075
See application file for complete search history.

(56) References Cited

U.S. PATENT DOCUMENTS

| | | |
|---|---|---|
| 5,012,503 A | 4/1991 | Nambu et al. |
| 7,968,050 B2 | 6/2011 | Vogt et al. |
| 8,653,319 B2 | 2/2014 | Amery et al. |
| 8,721,963 B2 | 5/2014 | Matthews et al. |
| 8,951,574 B2 | 2/2015 | Gehri et al. |
| 9,198,997 B2 | 12/2015 | Myntti et al. |
| 9,694,037 B2 | 7/2017 | Nataraj et al. |
| 2012/0253071 A1 | 10/2012 | Rau et al. |
| 2013/0116571 A1 | 5/2013 | Cox et al. |
| 2016/0145567 A1 | 5/2016 | Henry et al. |
| 2016/0304832 A1 | 10/2016 | Hariri et al. |

FOREIGN PATENT DOCUMENTS

| | | |
|---|---|---|
| CN | 102250390 A | 11/2011 |
| WO | 200005257 A1 | 2/2000 |
| WO | 2005014774 A1 | 2/2005 |
| WO | 2014209865 A1 | 12/2014 |
| WO | 2016200888 A2 | 12/2016 |

OTHER PUBLICATIONS

Champagne et al. Bioscience Microflora, 1996, 15(1):9-15.*
Leo et al. Biotechnol. Prog., 1990,6:51-53.*
Santagapita et al. Biomacromolecules, 2011, 12:3147-3155.*
Gunter et al. Carbohydrate Polymers, 2014, 103:550-557.*
Munarin et al. Food Hydrocolloids, 2013, 31:74-84.*
Fang, Y. et al., "Rehydration of Dried Alginate Gel Beads: Effect of the Presence of Gelatin and Gum Arabic." Carbohydrate Polymers, vol. 86, pp. 1145-1150, Jun. 13, 2011.
International Search Report and Written Opinion of the International Searching Authority; PCT/US2016/036464; dated Aug. 2, 2016; 11 Pages; European Patent Office.
Santagapita, P. et al., "Formulation and Drying of Alginate Beads for Controlled Release and Stabilization of Invertase." Biomacromolecules vol. 12, pp. 3147-3155, Aug. 18, 2011.
Vreeker, R. et al., "Drying and Rehydration of Calcium Alginate Gels." Food Biophysics, vol. 3, pp. 361-369, Jun. 26, 2008.
Da Violante et al; "Evaluation of the Cytotoxicity Effect of Dimethyl Sulfoxide (DMSO) on Caco2/TC7 Colon Tumor Cell Cultures" ; Biol. Pharm. Bull 25 (12) pp. 1600-1603 (2002.
Galvao et al; "Unexpected Low-Dose Toxicity of the Universal Solvent DMSO" ; The FASEB Journal, Research Communication, vol. 28, (2014); pp. 1-14.
Lee et al; "Toxicity Evaluation of Ethanol Treatment During In Vitro Maturation of Procine Oocytes and Subsequent Embroyonic Development Following Parthenogenetic Activation and In Vitro Fertilization" ; International Journal of Molecular Medicine; 34; pp. 1372-1380 (2014.
Oberdoerster et al; "Differential Effect of Ethanol on PC12 Cell Death" ; The Journal of Pharmacology and Experimental Therapeutics; vol. 287, No. 1; Paged 359-365 (1998.
Tapani et al; "Toxicity of Ethanol in Low Concentrations" ; Acta Radiologica; 37:6; pp. 923-926; (1996).
Japanese Patent Application No. 2017563565; Machine Translation of the Office Action dated Mar. 18, 2020; Japan Patent Office; 5 Pgs.
English Translation of CN201680033639.7 Office Action dated Jul. 17, 2020; 10 Pages; Chinese Patent Office.
Gong et al; "The Physical and Chemical Properties of Alginate and Its Application in Tissue Engineering Research and Clinical Application"; China Tissue Engineering Research and Clinical Rehabilitation, vol. 11, No. 18 pp. 3613-3615 (Abstract), 2007.

* cited by examiner

*Primary Examiner* — Bin Shen
(74) *Attorney, Agent, or Firm* — F. Brock Riggs

(57) ABSTRACT

A method of making a cell culture article is provided. The method includes forming a microcarrier from a microcarrier composition comprising a polygalacturonic acid compound or an alginic acid compound, infiltrating the microcarrier with a drying formulation to form an infiltrated microcarrier, and drying the infiltrated microcarrier to form a dried microcarrier, wherein the drying formulation comprises at least one of a saccharide and a monovalent cation.

11 Claims, 13 Drawing Sheets

DRYING FORMULATION FOR HYDROGEL MICROCARRIERS

This is a national stage application under 35 U.S.C. § 371 of International Application No. PCT/US2016/036464, filed on Jun. 8, 2016, which claims the benefit of priority under 35 U.S.C. § 119 of U.S. Provisional Application Serial No. 62/172,449 filed on Jun. 8, 2015 the content of which is relied upon and incorporated herein by reference in its entirety.

BACKGROUND

Field

The present disclosure relates generally to drying formulations for hydrogel microcarriers, and more specifically to methods for drying, sterilizing and re-hydrating hydrogel microcarriers.

Technical Background

In contrast to cell culture on flat surfaces where adhesive cells can reach high confluence and thus limit cell expansion via cell-to-cell contact inhibition, spherically-shaped microcarriers having a high ratio of surface area/volume present an attractive platform for efficient cell culture scale-up or expansion where either harvested cells or conditioned media can be the desired product.

Carboxyl-containing polysaccharides, such as polygalacturonic acid and alginic acid, can be crosslinked with divalent ions such as calcium cations to form stable hydrogels, which can be used in the form of beads as a substrate for cell culture or as an encapsulant for living cells.

The crosslinked hydrogels can be digested (at least partially dissolved) by removing the calcium such as with EDTA. This facilitates cell release without using proteinases, which can have an adverse effect on cell physiology.

Gamma sterilization, due to its process efficiency and depth of penetration, may be used to disinfect hydrogel microcarriers. However, the presence of water or humidity during gamma sterilization creates undesired free radicals, which can damage cells. It is thus contemplated that hydrogel microcarriers be dried prior to sterilization and then rehydrated after sterilization. Further, compared to wet hydrogels, gel material in a dried format is easier and more economical to package, ship and store.

In view of the foregoing, it would be advantageous to provide a low-cost and efficient method to dry, sterilize, and then fully rehydrate hydrogel microcarriers where the rehydrated microcarriers exhibit their initial geometry and mechanical properties.

BRIEF SUMMARY

In accordance with embodiments of the present disclosure, methods enable drying and complete rehydration of hydrogel beads such as beads made from polygalacturonic acid or alginic acid. In their dried state the beads may be sterilized such as by exposure to radiation. Complete rehydration occurs in minutes and the rehydrated beads exhibit their original (pre-dehydration) geometry and mechanical properties.

According to an embodiment of the present disclosure, prior to dehydrating, the beads are soaked in a drying formulation including a high concentration of mono- or poly-saccharides. According to another embodiment of the present disclosure, prior to dehydrating, the beads are soaked in a formulation including a monovalent cation and a low concentration of mono- or poly-saccharides. According to yet another embodiment of the present disclosure, prior to dehydrating, the beads are soaked in a formulation including a monovalent cation. Each of the embodiments disclosed herein enable gamma sterilization and subsequent rehydration of the beads for cell culture applications.

A method of making a cell culture article includes forming a microcarrier from a microcarrier composition such as a polygalacturonic acid compound or an alginic acid compound, infiltrating the microcarrier with a drying formulation, and drying the infiltrated microcarrier. The drying formulation includes at least one of a saccharide and a monovalent cation.

A cell culture article includes a polygalacturonic acid compound or an alginic acid compound and a drying formulation selected from the group consisting of a saccharide and a monovalent cation. In embodiments, the cell culture article is free of water.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 2:
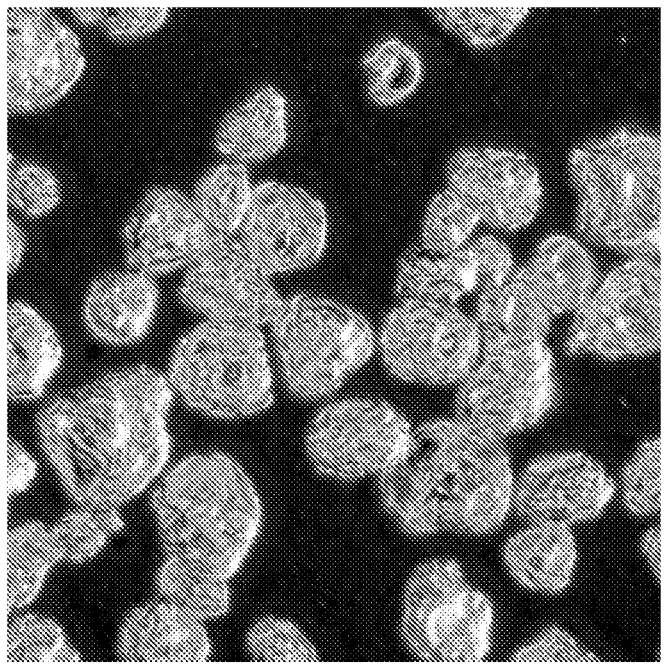
FIG. 2 is a phase contrast image of rehydrated PGA beads dried without excipient.

Reference will now be made in greater detail to various embodiments of the subject matter of the present disclosure, some embodiments of which are illustrated in the accompanying drawings. The same reference numerals will be used throughout the drawings to refer to the same or similar parts.

The drying of polysaccharide hydrogel beads (crosslinked by calcium) enables their sterilization for biotechnology applications such as large scale cell culture. Following sterilization, the beads are rehydrated and returned to their original (pre-dried) geometry and properties. For beads formed from PGA or alginic acid, crosslinking manifests between saccharide repeat units and calcium ions. This crosslinking is reversible, however, such as via removal of calcium by EDTA.

During traditional drying, the crosslinking density increases as carboxyl groups in the PGA or alginic acid get closer together. This prevents the polymer from rehydrating back to its original hydrogel state. It is believed that the addition of sodium or other cation to the rehydration solution increases the degree of rehydration, i.e., by breaking the newly-formed crosslinked structure. However, sodium addition to the rehydration solution also disrupts the original crosslinked structure and leads to continuous swelling and an attendant change in the network structure and associated properties.

Methods for forming hydrogel beads are disclosed in commonly-assigned International Application No. PCT/US2014/043624, and in U.S. Patent Application No. 62/172,299, the contents of which are incorporated by reference herein in their entirety.

Disclosed are methods for effectively dehydrating and rehydrating hydrogel beads. The methods involve treating the hydrogel beads prior to their dehydration.

According to an embodiment of the present disclosure, prior to dehydrating, the beads are infiltrated with a formulation including a high (e.g., 5-50 wt. %) mono- or poly-saccharide concentration. According to another embodiment, prior to dehydrating the beads are infiltrated with a formulation including a monovalent cation (e.g., 10-500 mM) and a low (e.g., 1-50 wt. %) concentration of mono- or poly-saccharide. According to yet another embodiment, prior to dehydrating, the beads are infiltrated with a formulation including a monovalent cation (e.g., 10-500 mM). Saccharide and/or the monovalent cation) are retained in the beads in their dried state. Example saccharides include glucose and sucrose as well as combinations thereof. Example monovalent cations include sodium, potassium and ammonium ions and combinations thereof. Each of the embodiments described herein enable gamma sterilization of the dried beads and their subsequent rehydration for cell culture applications.

According to embodiments of the present disclosure, each of the formulations described herein may further include a non-volatile liquid material. The non-volatile liquid material may be, for example, but not limited to, DMSO or a low molecular weight polyethylene glycol, such as PEG-400. The formulation may include between about 0.1 mL and about 2.0 mL per 100 mL of beads of the non-volatile liquid material. For example, the formulation may include between about 0.5 mL and about 1.5 mL per 100 mL of beads of the non-volatile liquid material, including ranges between any of the foregoing values.

During infiltration, the formulation is incorporated into the beads, e.g., via diffusion. The formulation may be homogeneously or non-homogeneously distributed throughout the beads. For instance, a concentration of saccharide or monovalent cation may be higher near the surface of the beads than at the center.

The infiltration may include soaking the beads in the formulation, e.g., for a time effective to incorporate the formulation into the beads prior to drying. In such an approach, the infiltration and the drying are performed in succession. In an alternate embodiment, infiltration of the formulation into the beads and drying of the beads may occur contemporaneously such as by spray drying.

Spray drying is a method of producing a dry powder from a liquid or slurry by rapidly drying with a hot gas. Spray dryers use an atomizer or spray nozzle to disperse the liquid or slurry. A hot drying gas can be passed as a co-current or counter-current flow to the atomizer. In embodiments, a PGA solution and drying formulation can be spray dried to simultaneously or contemporaneously form the microcarrier beads, incorporate the drying formulation into the beads and dry the beads.

In embodiments the wet microcarrier beads have an average particle size ranging from 50 to 500 micrometers, e.g., 50, 100, 200, 300, 400 or 500 micrometers, including ranges between any of the foregoing values. Microcarrier beads infiltrated with saccharide can include 1 to 50 wt. % saccharide, e.g., 1, 2, 5, 10, 20, 30, 40 or 50 wt. %, including ranges between any of the foregoing values. Microcarrier beads infiltrated with a monovalent cation can include 10 to 500 mM cation, e.g., 10, 20, 50, 100, 200, 300, 400 or 500 mM, including ranges between any of the foregoing values. Microcarrier beads infiltrated with both saccharide and a monovalent cation can include any composition of the drying formulation contemplated by the foregoing values, e.g., 1 to 20 wt. % glucose and 10 to 100 mM sodium cation.

As a dried powder, the beads typically form agglomerates having an agglomerated particle size (secondary particle size) ranging from 10 to 200 micrometers, e.g., 10, 20, 50, 100 or 200 micrometers, including ranges between any of the foregoing values. With the water extracted from the microcarriers, the drying formulation will account for a greater proportion of their overall composition. The dried powder is free of water, i.e., is dry to a water content of at most 10 wt. % (e.g., at most 1, 2, 4, 5 or 10 wt. % including ranges between any of the foregoing values).

In embodiments, dried microcarrier beads include 10 to 99 wt. % saccharide, e.g., 10, 20, 30, 40, 50, 60, 70, 80, 90, 95, 97, 98 or 99 wt. %, including ranges between any of the foregoing values. In embodiments, dried microcarrier beads include 0.5 to 20 wt. % monovalent cation, e.g., 0.5, 1, 2, 5, 10 or 20 wt. %, including ranges between any of the foregoing values. Microcarrier beads infiltrated with both saccharide and a monovalent cation when dried can include any composition of the drying formulation contemplated by the foregoing values, e.g., 60 to 80 wt. % saccharide and 0.5 to 10 wt. % monovalent cation.

EXAMPLES

Example 1—Drying and Rehydrating PGA Beads

PGA beads were synthesized by gelation and crosslinked with calcium using a method disclosed in commonly-assigned International Publication No. WO2014/209865, the contents of which are incorporated herein by reference in their entirety.

A 2% polygalacturonic acid (PGA) solution in water is mixed with calcium carbonate to form an aqueous suspension. The suspension is dispersed into heptane with Span 85 as a surfactant to form a water-in-oil emulsion. Acetic acid is added to the emulsion to dissolve the calcium carbonate and release calcium ions to crosslink the PGA molecules. A solution of $CaCl_2$ in ethanol is used to further strengthen the beads by introducing additional calcium ions into the crosslinked network. The diameter of the PGA beads ranges from 100 micrometers to 300 micrometers.

In advance of drying, the PGA beads are soaked in water or aqueous solutions containing different concentrations of glucose and/or NaCl for 2 hr. Through a filter (106 micrometer pore size) the beads are rinsed with isopropyl alcohol to remove excess soaking solution and pre-dehydrate the beads. The thus treated beads are then dried under vacuum for 24 h. The dried beads are characterized as an opaque, white powder.

The dried beads are rehydrated in water (5 min. agitation for a total swelling time of 10 min or 24 hr). The morphology of the rehydrated beads is observed under optical microscopy.

The pre-dehydration processing and rehydration results are summarized in Table I.

TABLE I

| # | Pre-dehydration treatment | Rehydration | Result |
|---|---|---|---|
| 1 | n/a | n/a | |
| 2 | water | $Na^+$, $K^+$ or $Mg^{2+}$ | Loss of original cross-linking; continuous swelling |
| 3 | 5% glucose | water | Partial rehydration |
| 4 | 20% glucose | water | Partial rehydration |
| 5 | 40% glucose | water | Complete rehydration |
| 6 | 50 mM NaCl | water | Partial rehydration |
| 7 | 50 mM NaCl + 5% glucose | water | Complete rehydration |

Figure 1:
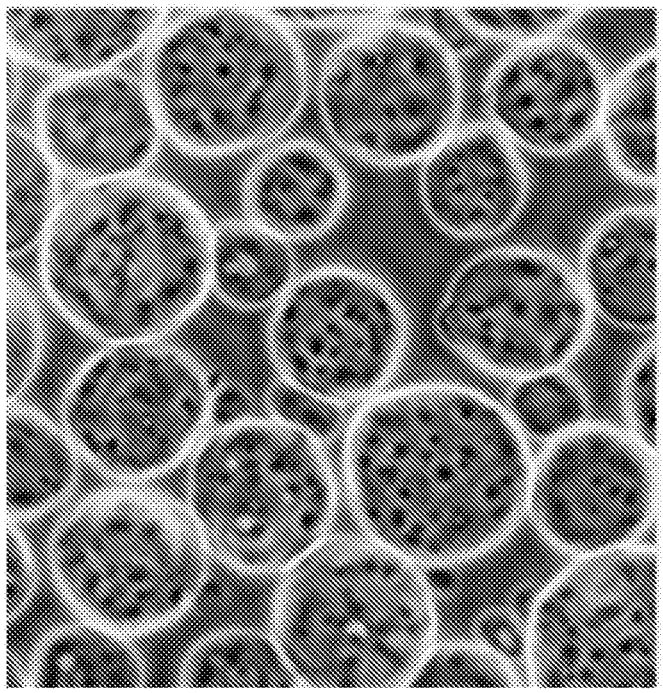
FIG. 1 is a phase contrast image of PGA beads crosslinked with calcium.
Figure 4:
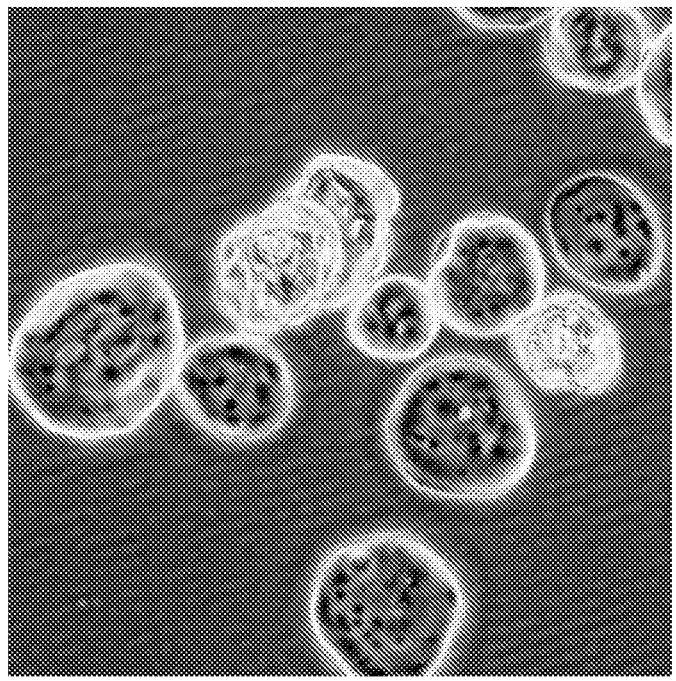
FIG. 4 is a phase contrast image of rehydrated PGA beads dried with 20% glucose.
Figure 3:
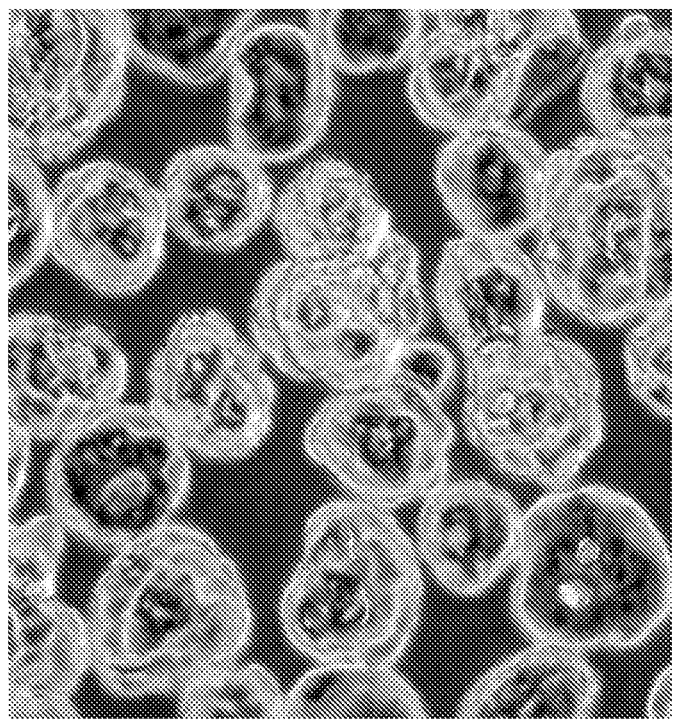
FIG. 3 is a phase contrast image of rehydrated PGA beads dried with 5% glucose.
Figure 5:
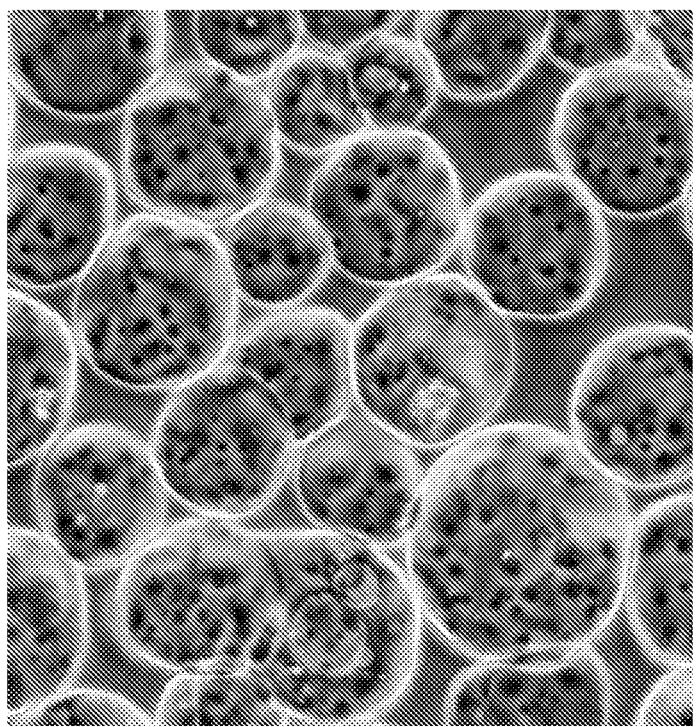
FIG. 5 is a phase contrast image of rehydrated PGA beads dried with 40% glucose.

FIGS. 1-7 are phase contrast images of calcium-cross-linked PGA beads. A control image of the beads before drying is shown in FIG. 1 (Sample 1). FIG. 2 is an image of rehydrated beads soaked only in water prior to drying (Sample 2). The rehydration is clearly incomplete. Rehydration of the dried beads improves proportional to the amount of glucose incorporated into the beads as seen in FIGS. 3-5. Partial rehydration is realized following treatment with 5% and 20% glucose (Samples 3 and 4), though even after 24 h these beads fail to recover their original size and morphology. Complete rehydration is realized for beads treated with 40% glucose as seen in FIG. 5. The Sample 5 beads rehydrate to their original size and morphology in 15 min.

Figure 6:
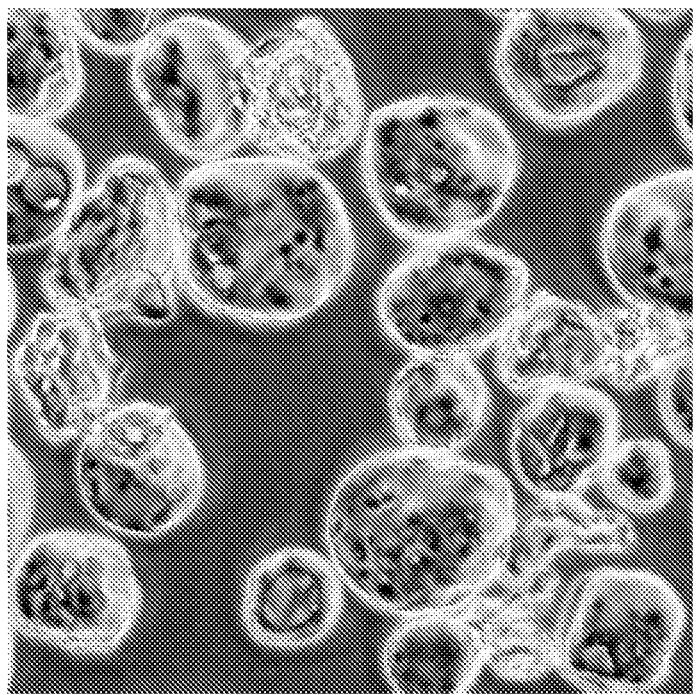
FIG. 6 is a phase contrast image of rehydrated PGA beads dried with 50 mM NaCl.
Figure 7:
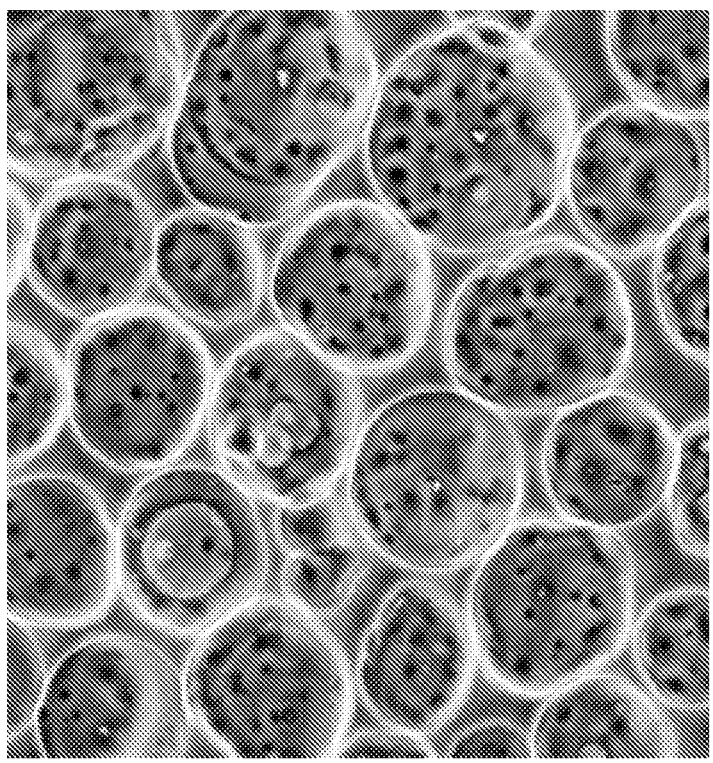
FIG. 7 is a phase contrast image of rehydrated PGA beads dried with 5% glucose and 50 mM NaCl.

FIG. 6 is an image of rehydrated beads soaked in 50 mM NaCl prior to drying (Sample 6). These dried beads partially rehydrate. However, as shown in FIG. 7, if 5% glucose is combined with the 50 mM NaCl solution prior to drying, the beads completely rehydrate in 15 min and maintain their size and morphology during extensive soaking.

Example 2—Drying of Coated PGA Beads for Cell Culture

Synthemax®-SC Coating:

30 ml of 0.25 mg/ml Synthemax®-SC solution is added to a plastic centrifuge tube containing 7.5 ml packed PGA beads prepared as described in Example 1. After gentle agitation, the tube is heated in an oven at 40° C. for 30 min and cooled to 23° C. The thus coated-beads are rinsed three times with 40 ml water and centrifuged to discard the supernatant. Thereafter, the wet beads are suspended in water and stored at 4° C. Coated beads without drying are used as a control.

Drying and Gamma Sterilization:

45 ml of either 339 g/l or 475 g/l glucose was added to 7.5 ml Synthemax®-coated beads prepared as described in the previous step. The suspension is placed in a 100 ml flask and agitated gently at 23° C. for 18 h to allow the glucose to diffuse into the beads. After soaking, the glucose-infiltrated beads are washed 3 times with IPA to remove excess soaking solution and partially dehydrate the beads. The beads are then dried under vacuum for 16 h to produce a powder. The powder is packed in glass vials under nitrogen for gamma irradiation at 19-21 kilogray (kGy). Before cell culture, the gamma-sterilized beads having the Synthemax®-SC surface are rehydrated with water for 30 min and rinsed one time with water.

Cell Culture:

2 ml wet rehydrated beads are added to a 125 ml disposable spinner flask with 25 ml Mesencult XF medium and seeded with about 1 million bone marrow-derived hMSCs (STEMCELL™ Technologies (SCT), Cat. No. MSC-001F, BM ID#2637). The flask is left undisturbed overnight to allow cell attachment. Thereafter, the seeded microcarriers are submitted to intermittent agitation for 7 days in a humidified incubator (37° C. and 5% $CO_2$). A full medium exchange is performed at day 4.

After 7 days, the cultured cells are harvested by first rinsing the microcarriers with D-PBS, and then dissolving the microcarriers via the addition of a solution comprising 10 ml 50 U pectinase and 5 mM ETDA. The total number of cultured cells is obtained by counting using a hemocytometer after trypan blue staining. Fold expansion is calculated based on the initial cell seeding density and the final cell density at day 7. The coated beads without drying are sanitized with 70% ethanol and used as controls during cell culture.

Figure 8:
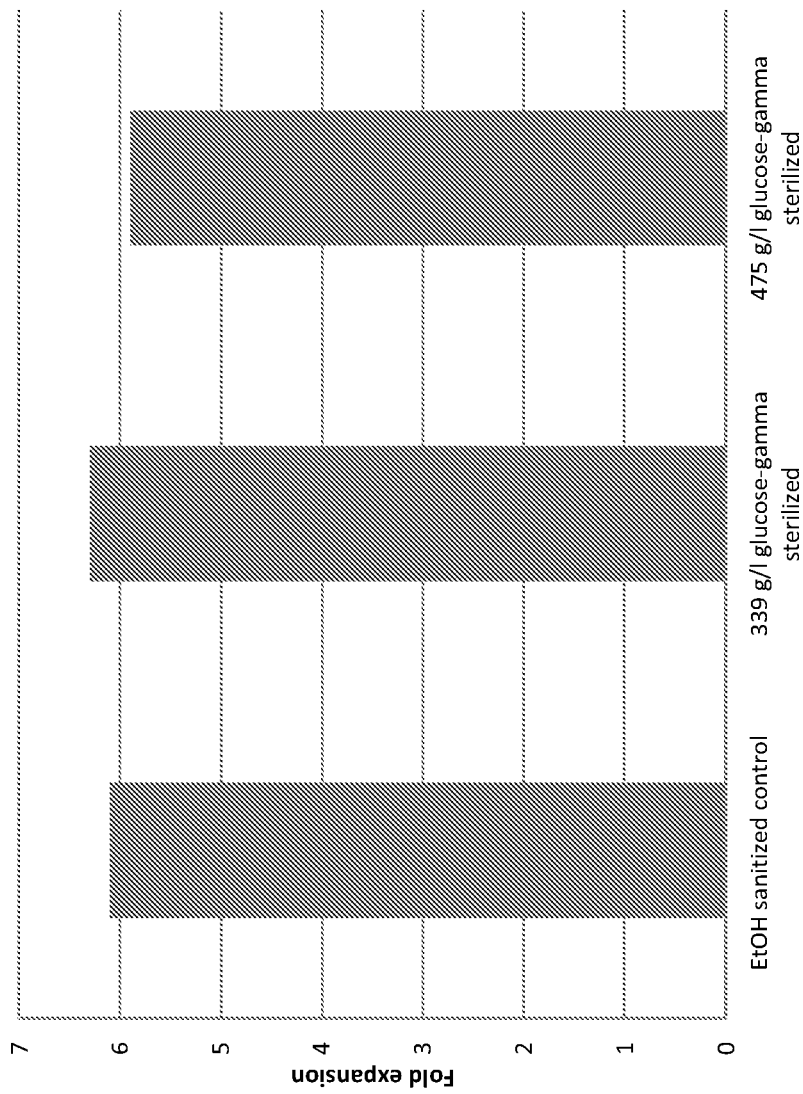
FIG. 8 is a graph of fold expansion for hMSCs cultured on PGA microcarriers.

As seen with reference to FIG. 8, PGA beads infiltrated with a high concentration of glucose (339 or 475 g/l) support drying, gamma-sterilization, rehydration, and efficient hMSC expansion in stirred culture and serum-free medium. A six-fold expansion is achieved within 7 days, which is comparable to the results achieved with ethanol-sanitized PGA beads.

Example 3—Drying of Coated PGA Beads for Cell Culture

Synthemax®-SC Coating:
A Synthemax®-SC solution is mixed with a 20 ml PGA bead suspension (with 10 ml of packed beads) as in Example 2.

Drying and Gamma Sterilization:
The washed beads are soaked for 2 hr at 23° C. in a solution comprising 5% glucose and 125 mM NaCl. The soaked beads are rinsed in 70 ml IPA to remove excess glucose and NaCl and to partially dehydrate the beads. The beads are then dried under vacuum for 24 h to produce a powder. The powder is packed in glass vials under nitrogen for gamma irradiation at 19-21 kGy.

Cell Culture:
Before cell culture, the gamma-sterilized beads with the Synthemax®-SC surface are rehydrated with water for 30 min. The supernatant is then replaced with 10% serum-containing medium and transferred into 125 mL spinner flasks for seeding with Human Bone Marrow-Derived Mesenchymal Stem Cells (hBMSCs) ($1 \times 10^6$ cells per 1.8 ml of packed beads in 50 ml of medium, which corresponding to 5,500 cells/cm$^2$).

After 6 days, the cells are stained with Calcein acetomethoxy (AM) and fluorescence images are taken. The total number of cultured cells is obtained by dissolving the beads in a solution comprising 10 ml 50 U pectinase and 5 mM ETDA. The cells are counted using a Vi-CELL® cell counter. Fold expansion is calculated based on the initial cell seeding density and the final cell density at day 6. Coated beads without drying are sanitized with an autoclave and used as controls during cell culture.

Figure 9:
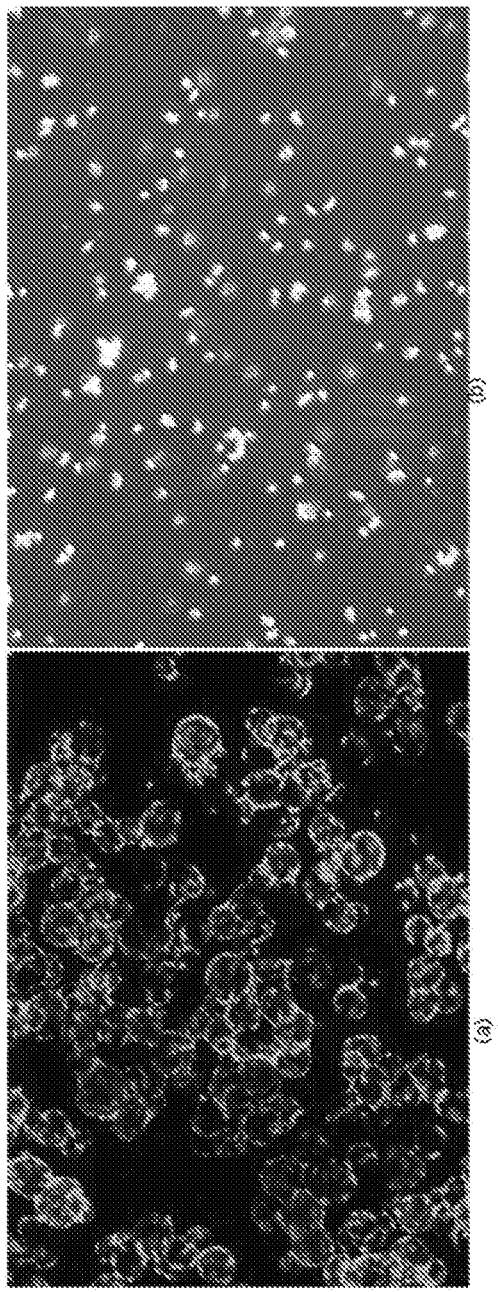
FIGS. 9A-9D show Calcein acetomethoxy (AM)-stained fluorescence images of PGA microcarriers according to embodiments.
Figure 9:
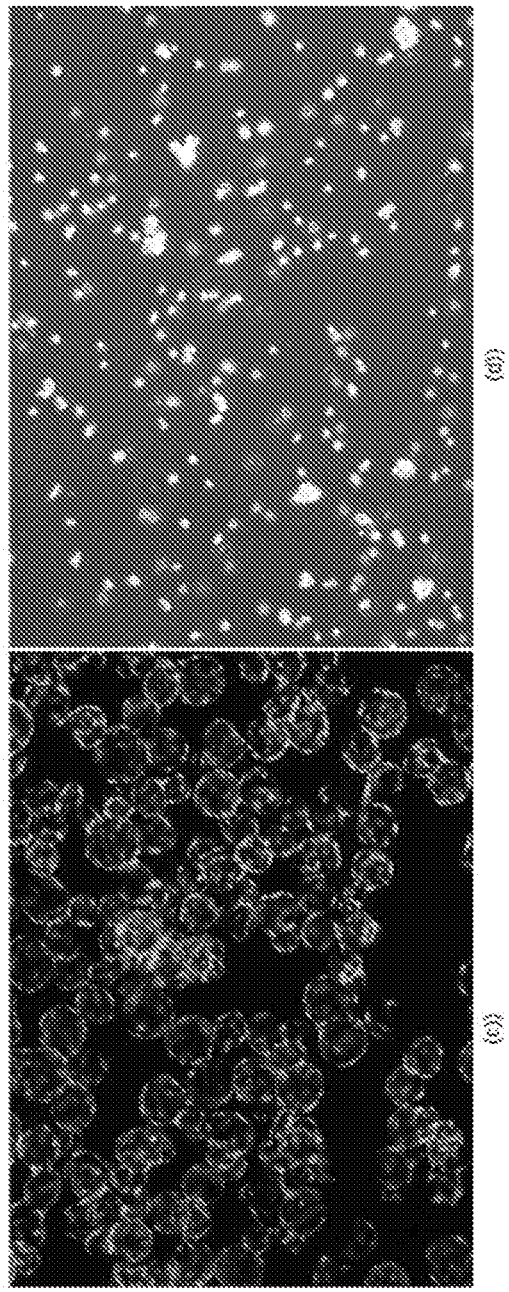

Calcein AM stained fluorescence images of Synthemax®-SC surface-coated beads after 6 days in culture are shown in FIG. 9A (gamma sterilized beads) and FIG. 9c (autoclave sterilized beads). As seen in FIG. 9A, the hBMSC cells attach, spread, and grow on the gamma-sterilized PGA beads. This is comparable to beads sterilized using conventional autoclaving as shown in FIG. 9C (comparative).

The microcarriers are easily digested with pectinase/EDTA solution, releasing the hBMSC cells into solution. Phase contrast microscopic images of single cell solutions comprising hBMSCs at day 6, after digestion of the microcarriers with pectinase/EDTA, are shown in FIG. 9B (gamma sterilized beads) and FIG. 9D (autoclave sterilized beads) (comparative).

Figure 10A:
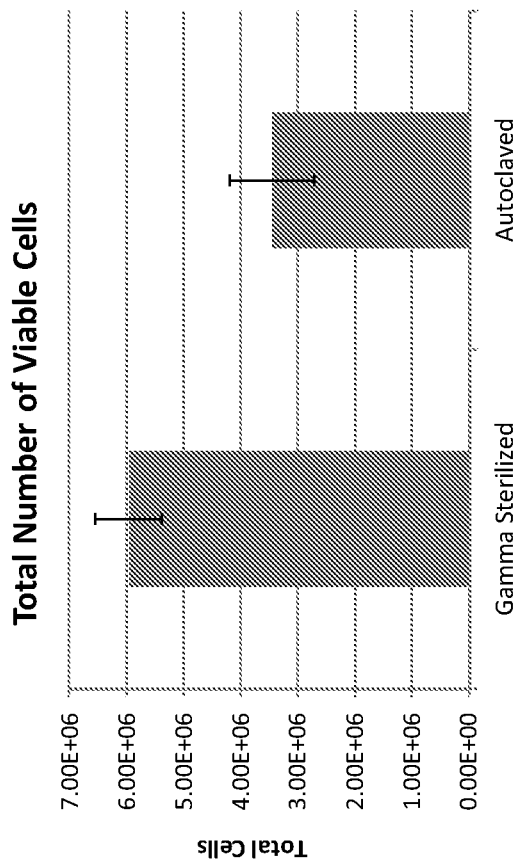
FIGS. 10A and 10B are graphs depicting the total number of recovered cells and the percentage of viable cells recovered from gamma-sterilized and autoclave-sterilized PGA microcarriers.
Figure 10B:
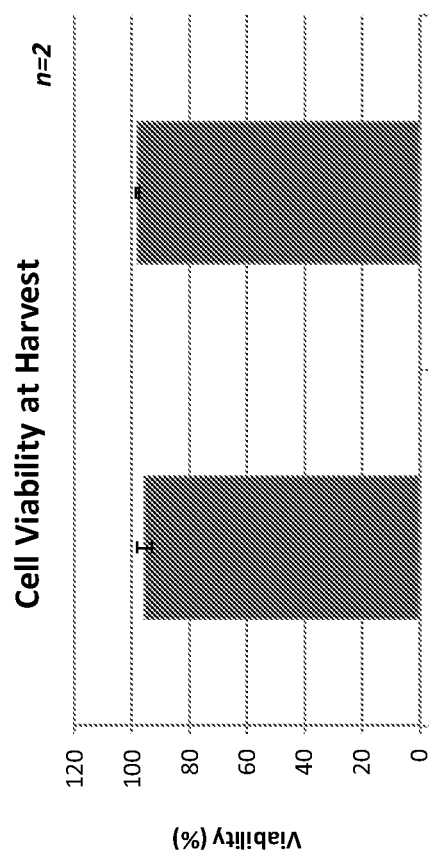

With reference to FIG. 10, the growth and viability of hBMSCs seeded and cultured on gamma sterilized PGA microcarriers was comparable to that for the autoclave sterilized beads. As shown in FIG. 10A, the total cell number at harvest evidences a 6 fold expansion of cells after 6 days of culture. Further, over 90% of these cells were viable, as shown in FIG. 10B. The values in FIG. 10 are the average±the standard deviation of two samples tested per sterilization condition.

Example 4—Drying of Coated PGA Beads for Cell Culture

Synthemax®-SC Coating:
A Synthemax®-SC surface coating solution is mixed with a 20 ml PGA bead suspension (with 10 ml of packed beads) as in Example 2.

Drying and Gamma Sterilization:
The washed beads are soaked for 2 hr at 23° C. in a solution comprising 5% glucose and 125 mM NaCl. The soaked beads are rinsed in 70 ml IPA to remove excess glucose and NaCl and to partially dehydrate the beads. The beads are then dried under vacuum for 24 h to produce a powder. The powder is packed in glass vials under nitrogen for gamma irradiation at 19-21 kGy.

Cell Culture:
Vero cells (ATCC® CCL-81™) are cultured in DMEM (Corning, Cat. No. 10-013) supplemented with 5% FBS (Corning, Cat. No. 35-010), 1×MEM NEAA (Corning, Cat. No. 25-025) and 2 mM L-glutamine (Corning, Cat. No. 25-005). Before cell culture, the gamma-sterilized beads having a Synthemax®-SC coated surface are rehydrated with water for 30 min. The supernatant is then replaced with serum-containing medium and transferred into 125 mL spinner flasks for seeding with the Vero cells at approximately 15,000 cells/cm$^2$.

After 6 days, the cells are stained with Calcein AM and imaged with fluorescence microscopy. The total number of cultured cells is obtained by dissolving the beads in a solution comprising 10 ml 50 U pectinase and 5 mM ETDA. The cells are counted using a Vi-CELL® cell counter. Beads processed without drying, having a Synthemax®-SC surface, and sanitized with ethanol and are used as controls.

Figure 11B:
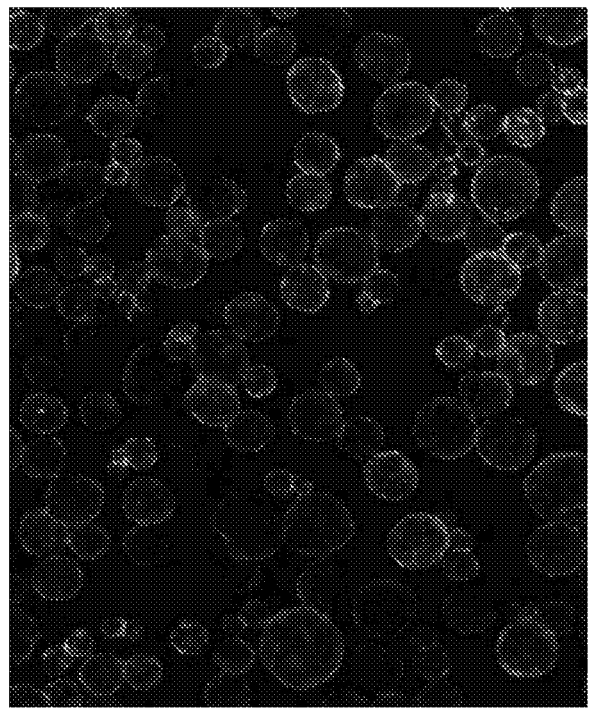
FIGS. 11A and 11B are Calcein acetomethoxy (AM)-stained fluorescence images of Vero cells on PGA microcarriers having a Corning Incorporated Synthemax®-SC surface.
Figure 11A:
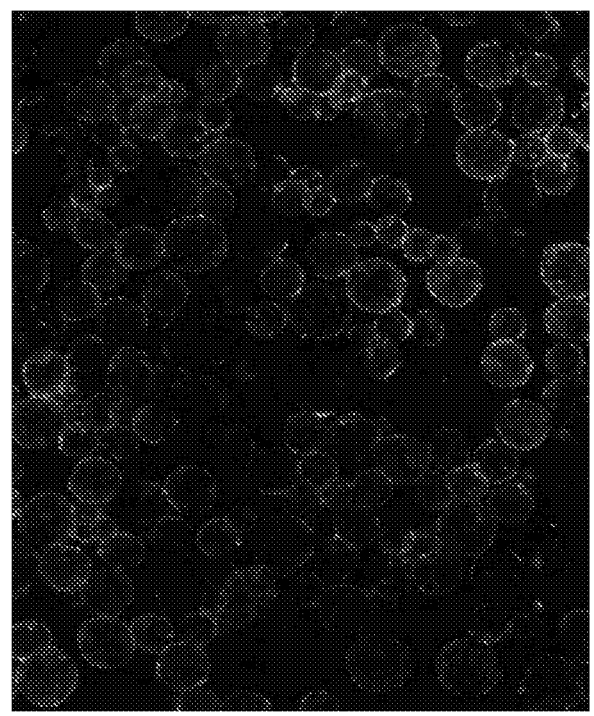
Figure 12:
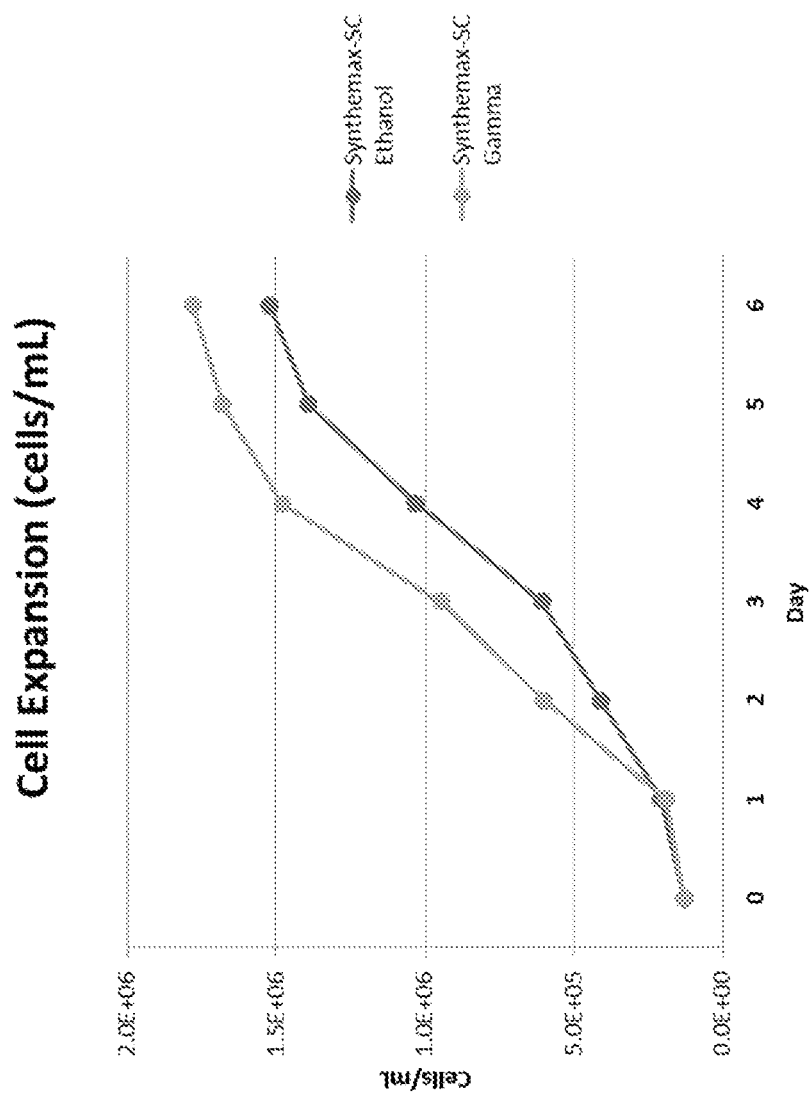
FIG. 12 is a graph of cell density versus culture time.

Calcein AM stained fluorescence images of beads having a Synthemax®-SC surface after 4 days in culture are shown in FIG. 11. Attachment of the Vero cells to beads sanitized with ethanol (FIG. 11A, comparative) is comparable to the attachment of the gamma-sterilized and rehydrated PGA beads (FIG. 11B). With reference to FIG. 12, the number of cells on the gamma-sterilized and rehydrated PGA beads after 6 days of culture exceeds the number of cells on the un-dried, ethanol-sterilized beads. As illustrated, the instant drying formulation enables PGA beads to be dried, gamma sterilized, and maintain biological performance.

Example 5—Drying and Rehydrating with Different Concentrations of NaCl Solutions and DMSO PGA beads were synthesized by gelation and crosslinked with calcium using a method disclosed in commonly-assigned U.S. Patent Application No. 62/172,299.

A 1.75% PGA solution in water is dropped through a nozzle and into a 4.0% calcium carbonate solution to form a crosslinked bead. The beads are then washed with water to remove any excess calcium.

In advance of drying, the PGA beads are soaked in aqueous solutions containing different concentrations of NaCl for 1 hr. Through a filter (106 micrometer pore size) the beads are rinsed with isopropyl alcohol to remove excess soaking solution and pre-dehydrate the beads. The beads are then placed in a flask and 1.0 mL of DMSO is added to the flask for each 100 mL of beads. The beads were then dried using a rotary evaporator. The dried beads are characterized as an opaque, white powder.

The dried beads are rehydrated in water, where 8.0 mL of water is added to the dried beads for every 50 mg of dried powder and mixed. Rehydration was observed to be complete within 2.0 minutes or less. The morphology of the rehydrated beads is observed under optical microscopy.

The pre-dehydration processing and rehydration results are summarized in Table II.

TABLE II

| # | Pre-dehydration treatment | Rehydration | Bead Size | Result |
|---|---|---|---|---|
| 8 | n/a | n/a | 258 ± 7 μm | |
| 9 | 500 mM NaCl + DMSO | water | 307 ± 8 μm | Complete rehydration - over swelling |
| 10 | 125 mM NaCl + DMSO | water | 256 ± 5 μm | Complete rehydration |
| 11 | 50 mM NaCl + DMSO | water | 192 ± 9 μm | Partial rehydration |
| 12 | None | water | 125 ± 10 μm | Partial rehydration |

Figure 14:
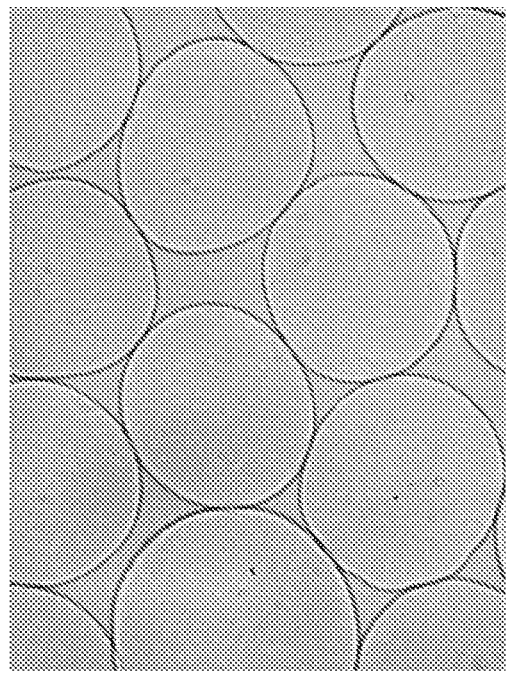
FIG. 14 is an image of rehydrated PGA beads dried with 500 mM NaCl and 1.0 mL DMSO.
Figure 13:
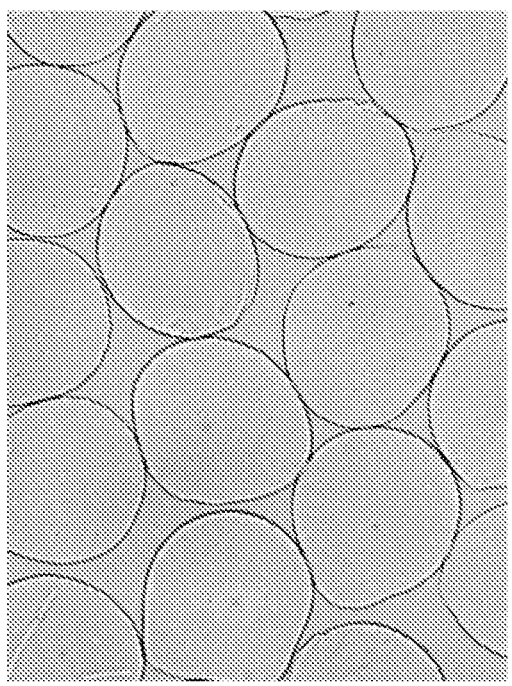
FIG. 13 is an image of PGA beads crosslinked with calcium.
Figure 16:
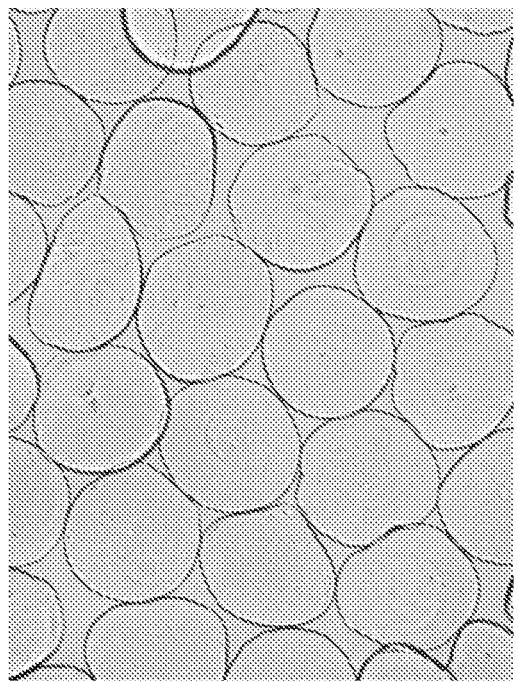
FIG. 16 is an image of rehydrated PGA beads dried with 50 mM NaCl and 1.0 mL DMSO.
Figure 15:
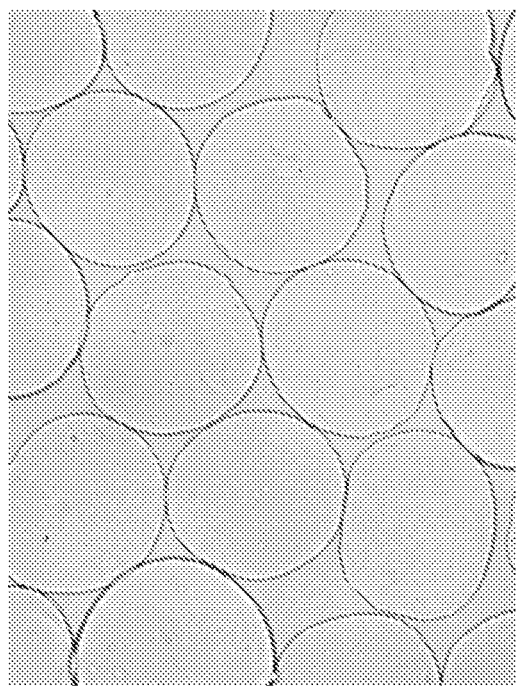
FIG. 15 is an image of rehydrated PGA beads dried with 125 mM NaCl and 1.0 mL DMSO.
Figure 17:
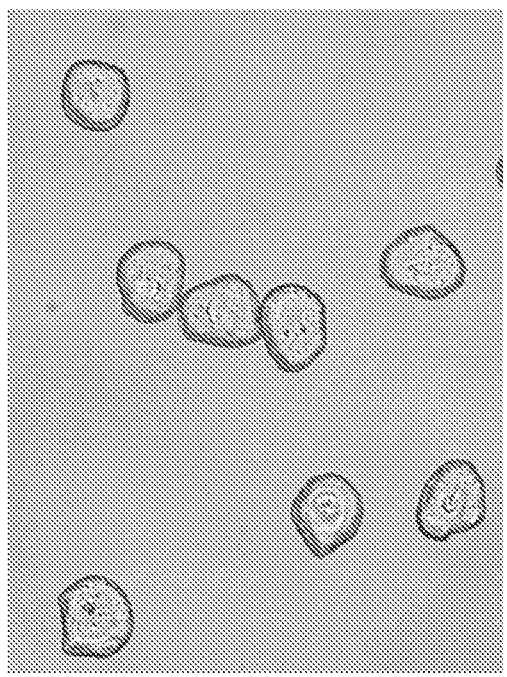
FIG. 17 is an image of rehydrated PGA beads dried without excipient.

FIGS. 13-17 are phase contrast images of calcium-cross-linked PGA beads formed in the present example. A control image of the beads before drying is shown in FIG. 13 (Sample 8). The beads in FIG. 13 were determined to have a size of 258±7 μm. FIG. 14 is an image of rehydrated beads soaked in 500 mM NaCl prior to drying (Sample 9). Complete rehydration is realized for the beads shown in FIG. 14, though over swelling of the beads was observed as the beads were determined to have a size of 307±8 μm. FIG. 15 is an image of rehydrated beads soaked in 125 mM NaCl prior to drying (Sample 10). Complete rehydration and swelling to the original bead size and morphology is realized for the beads shown in FIG. 15 as the beads were determined to have a size of 256±5 μm. FIG. 16 is an image of rehydrated beads soaked in 50 mM NaCl prior to drying (Sample 11). Rehydration of the beads in FIG. 16 is incomplete as the beads were determined to have a size of 192±9 μm. FIG. 17 is an image of rehydrated beads that were not soaked prior to drying (Sample 12). Rehydration of the beads in FIG. 17 is clearly incomplete as the beads were determined to have a size of 125±10 μm.

Example 6—Drying and Rehydrating with NaCl Solutions and Different Volumes of DMSO PGA beads were synthesized as described in Example 5.

In advance of drying, the PGA beads are soaked in an aqueous solutions containing 125 mM NaCl for 1 hr. Through a filter (106 micrometer pore size) the beads are rinsed with isopropyl alcohol to remove excess soaking solution and pre-dehydrate the beads. The beads are then placed in separate flasks with each of the separate flasks having a different volume of DMSO added for each 100 mL of beads. The beads were then dried using a rotary evaporator. The dried beads are characterized as an opaque, white powder.

The dried beads are rehydrated in water, where 8.0 mL of water is added to the dried beads for every 50 mg of dried powder and mixed. Rehydration was observed to be complete within 2.0 minutes or less. The morphology of the rehydrated beads is observed under optical microscopy.

The pre-dehydration processing and rehydration results are summarized in Table III.

TABLE III

| # | Pre-dehydration treatment | DMSO Volume per 100 mL of Beads | Rehydration | Result |
|---|---|---|---|---|
| 13 | 125 mM NaCl | 0 mL | water | 30-50% of rehydrated beads had cracks |
| 14 | 125 mM NaCl + DMSO | 0.5 mL | water | Less than 30% of rehydrated beads had cracks |
| 15 | 125 mM NaCl + DMSO | 1.0 mL | water | Almost none of the rehydrated beads had cracks |

Figure 18:
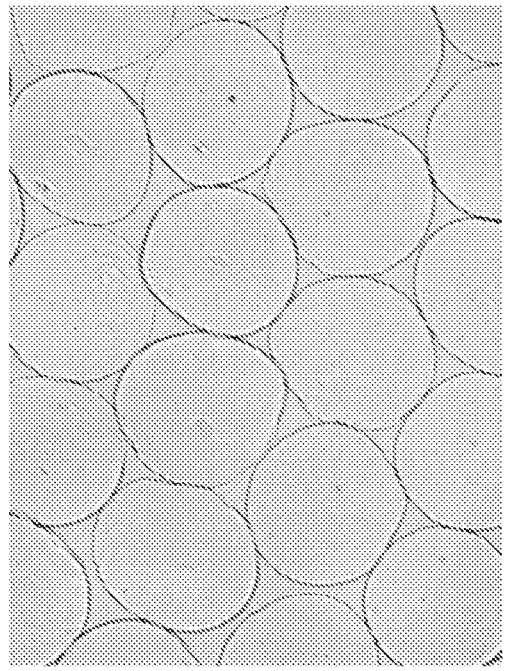
FIG. 18 is an image of rehydrated PGA beads dried with 125 mM NaCl.
Figure 20:
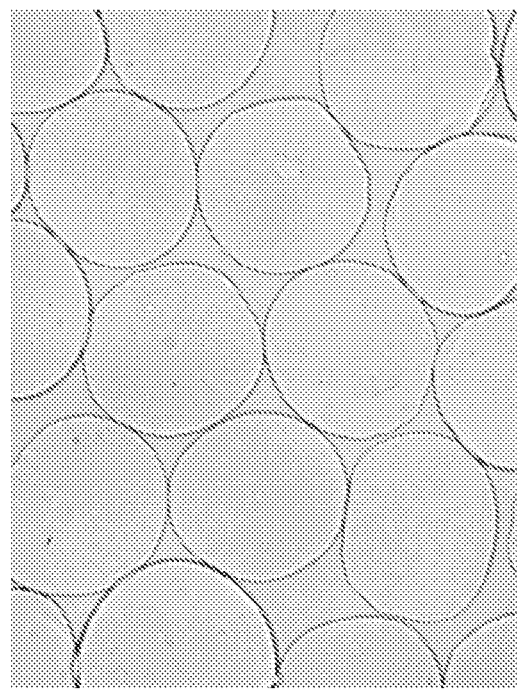
FIG. 20 is an image of rehydrated PGA beads dried with 125 mM NaCl and 1.0 mL DMSO.
Figure 19:
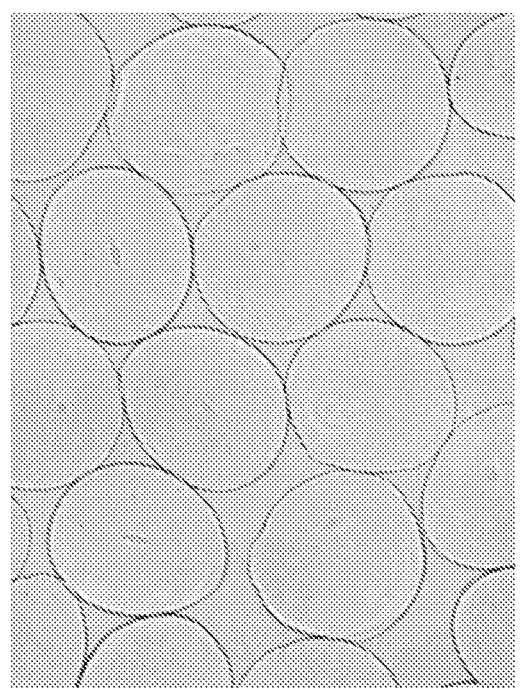
FIG. 19 is an image of rehydrated PGA beads dried with 125 mM NaCl and 0.5 mL DMSO.

FIGS. 18-20 are phase contrast images of calcium-cross-linked PGA beads formed in the present example. FIG. 18 is an image of rehydrated beads soaked in 125 mM NaCl, but not in DMSO, prior to drying (Sample 13). As shown in FIG. 18, 30-50% of the rehydrated beads were observed to have cracks. FIG. 19 is an image of rehydrated beads soaked in 125 mM NaCl and 0.5 mL DMSO prior to drying (Sample 14). While some of the beads were observed to contain cracks, cracking of the rehydrated beads of Sample 14 was observed to be reduced as compared to the rehydrated beads of Sample 13. FIG. 20 is an image of rehydrated beads soaked in 125 mM NaCl and 1.0 mL DMSO prior to drying (Sample 15). As shown in FIG. 20, almost none of the rehydrated beads of Sample 15 were observed to contain cracks. In other words, cracking of the rehydrated beads of Sample 15 was observed to be substantially reduced as compared to the rehydrated beads of Samples 13 and 14.

Without wishing to be bound by any particular theory, it is believed that cracking occurs as a result of rehydration because water is quickly absorbed by the beads and fast expansion of the beads occurs. An outer portion of a bead rehydrates slower than an inner portion of the bead and is believed to not possess enough elasticity to match the volume expansion of the bead. Including a non-volatile liquid material, such as DMSO or PEG-400, in the drying formulation provides a liquid material that can infiltrate the bead, remain the bead after drying and provide elasticity to the outer portion of the bead during rehydration. As such, during rehydration, the outer portion of the bead will be able to expand enough to match the increase of the volume of the inner portion of the bead and prevent cracking.

In embodiments, effective rehydration of dehydrated PGA beads can be achieved by treating the beads prior to dehydration with either a high concentration of a mono- or poly-saccharide (e.g., glucose), a combination of a low concentration of a mono- or poly-saccharide and a monovalent salt (e.g., sodium chloride), or a monovalent salt.

According to an aspect (1) of the present disclosure, a method of making a cell culture article is provided. The method comprises forming a microcarrier from a microcarrier composition comprising a polygalacturonic acid compound or an alginic acid compound, infiltrating the microcarrier with a drying formulation to form an infiltrated microcarrier, and drying the infiltrated microcarrier to form a dried microcarrier, wherein the drying formulation comprises at least one of a saccharide and a monovalent cation.

According to another aspect (2) of the present disclosure, the method according to aspect (1) is provided further comprising sterilizing the dried microcarrier to form a sterilized dried microcarrier.

According to another aspect (3) of the present disclosure, the method according to aspect (2) is provided wherein sterilizing the dried microcarrier comprises exposing the dried microcarrier to gamma radiation.

According to another aspect (5) of the present disclosure, the method according to any of aspects (1)-(4) is provided further comprising rehydrating the microcarrier.

According to another aspect (6) of the present disclosure, the method according to any of aspects (1)-(5) is provided, wherein infiltrating the microcarrier with a drying formulation comprises soaking the microcarrier in a solution of the drying formulation.

According to another aspect (7) of the present disclosure, the method according to any of aspects (1)-(5) is provided wherein infiltrating the microcarrier with a drying formulation comprises simultaneously spraying the microcarrier composition and the drying formulation.

According to another aspect (8) of the present disclosure, the method according to any of aspects (1)-(7) is provided wherein the drying formulation comprises 1 to 50 wt. % saccharide.

According to another aspect (9) of the present disclosure, the method according to any of aspects (1)-(8) is provided wherein the drying formulation comprises 10 to 500 mM monovalent cation.

According to another aspect (10) of the present disclosure, the method according to any of aspects (1)-(9) is provided wherein the drying formulation comprises 1 to 50 wt. % saccharide and 10 to 500 mM monovalent cation.

According to another aspect (11) of the present disclosure, the method according to any of aspects (1)-(10) is provided wherein the saccharide is selected from the group consisting of sucrose and glucose.

According to another aspect (12) of the present disclosure, the method according to any of aspects (1)-(11) is provided wherein the monovalent cation is selected from the group consisting of sodium, potassium and ammonium ions.

According to another aspect (13) of the present disclosure, the method according to any of aspects (1)-(12) is provided wherein the drying formulation comprises a non-volatile liquid material.

According to another aspect (14) of the present disclosure, the method according to aspect (13) is provided wherein the non-volatile liquid material is selected from the group consisting of DMSO and a low molecular weight polyethylene glycol.

According to another aspect (15) a cell culture article is provided. The cell culture article comprises: a polygalacturonic acid compound or an alginic acid compound and a drying formulation comprising at least one of a saccharide and a monovalent cation, wherein the cell culture article is free of water.

According to another aspect (16) of the present disclosure, the cell culture article according to aspect (15) is provided wherein the drying formulation comprises 1 to 50 wt. % saccharide.

According to another aspect (17) of the present disclosure, the cell culture article according to any of aspects (15)-(16) is provided wherein the drying formulation comprises 0.5 to 20 wt. % monovalent cation.

According to another aspect (18) of the present disclosure, the cell culture article according to any of aspects (15)-(17) is provided wherein the drying formulation comprises 1 to 50 wt. % saccharide and 0.5 to 20 wt. % monovalent cation.

According to another aspect (19) of the present disclosure, the cell culture article according to any of aspects (15)-(18) is provided wherein the drying formulation comprises a non-volatile liquid material.

According to another aspect (20) of the present disclosure, the cell culture article according to aspect (19) is provided wherein the non-volatile liquid material is selected from the group consisting of DMSO and a low molecular weight polyethylene glycol.

As used herein, the singular forms "a," "an" and "the" include plural referents unless the context clearly dictates otherwise. Thus, for example, reference to a "monovalent cation" includes examples having two or more such "monovalent cations" unless the context clearly indicates otherwise The term "include" or "includes" means encompassing but not limited to, that is, inclusive and not exclusive.

"Optional" or "optionally" means that the subsequently described event, circumstance, or component, can or cannot occur, and that the description includes instances where the event, circumstance, or component, occurs and instances where it does not.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a solution comprising a saccharide dissolved in a solvent include embodiments where a solution consists of a saccharide dissolved in a solvent and embodiments where a solution consists essentially of a saccharide dissolved in a solvent.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. A method of making a cell culture article, the method comprising the steps of:
   a) forming a microcarrier from a composition consisting of polygalacturonic acid and calcium;
   b) infiltrating the microcarrier with a drying formulation to form an infiltrated microcarrier, wherein the drying formulation comprises at least one of a saccharide or a monovalent cation;
   c) after infiltrating the microcarrier with the drying formulation, drying the infiltrated microcarrier to form a dried microcarrier, and
   d) sterilizing the dried microcarrier with gamma radiation to form a sterilized dried microcarrier.

2. The method according to claim 1, further comprising rehydrating the dried microcarrier.

3. The method according to claim 1, wherein infiltrating the microcarrier with a drying formulation comprises soaking the microcarrier in a solution of the drying formulation.

4. The method claim 1, wherein infiltrating the microcarrier with a drying formulation comprises simultaneously spraying the microcarrier composition and the drying formulation.

5. The method according to claim 1, wherein the drying formulation comprises 1 to 50 wt.% saccharide.

6. The method according to claim 1, wherein the drying formulation comprises 10 to 500 mM monovalent cation.

7. The method according to claim 1, wherein the drying formulation comprises 1 to 50 wt.% saccharide and 10 to 500 mM monovalent cation.

8. The method according to claim 1, wherein the saccharide is selected from the group consisting of sucrose and glucose.

9. The method according to claim 1, wherein the monovalent cation is selected from the group consisting of sodium, potassium and ammonium ions.

10. The method according to claim 1, wherein the drying formulation further comprises a non-volatile liquid material.

11. The method according to claim 10, wherein the non-volatile liquid material is selected from the group consisting of DMSO and a low molecular weight polyethylene glycol.

* * * * *

UNITED STATES PATENT AND TRADEMARK OFFICE
CERTIFICATE OF CORRECTION

PATENT NO. : 10,900,021 B2
APPLICATION NO. : 15/579776
DATED : January 26, 2021
INVENTOR(S) : Paula Jean Dolley-Sonneville et al.

Page 1 of 1

It is certified that error appears in the above-identified patent and that said Letters Patent is hereby corrected as shown below:

On the Title Page

Column 2, item [56], Line 19, delete "(2002." and insert -- (2002). --, therefor.

Column 2, item [56], Line 24, delete "Procine" and insert -- Porcine --, therefor.

Column 2, item [56], Line 24, delete "Embroyonic" and insert -- Embryonic --, therefor.

Column 2, item [56], Line 27, delete "(2014." and insert -- (2014). --, therefor.

Column 2, item [56], Line 30, delete "(1998." and insert -- (1998). --, therefor.

In the Claims

Column 14, Line 4, Claim 4, after "method" insert -- according to --.

Signed and Sealed this
Sixth Day of April, 2021

Drew Hirshfeld
*Performing the Functions and Duties of the
Under Secretary of Commerce for Intellectual Property and
Director of the United States Patent and Trademark Office*